US005534244A

United States Patent [19]

Tung

[11] Patent Number: 5,534,244
[45] Date of Patent: Jul. 9, 1996

[54] METHODS AND COMPOSITIONS FOR MINERALIZING AND/OR FLUORIDATING CALCIFIED TISSUES WITH AMORPHOUS STRONTIUM COMPOUNDS

[76] Inventor: Ming S. Tung, 15233 Falconbridge Ter., Gaithersburg, Md. 20878

[21] Appl. No.: 239,244

[22] Filed: May 6, 1994

Related U.S. Application Data

[60] Continuation-in-part of Ser. No. 104,350, Aug. 9, 1993, Pat. No. 5,437,857, which is a division of Ser. No. 723,839, Jul. 1, 1991, Pat. No. 5,268,167, which is a division of Ser. No. 356,201, May 24, 1989, Pat. No. 5,037,639.

[51] Int. Cl.$^6$ .............................. A61K 7/16; A61K 7/18; A61K 9/12
[52] U.S. Cl. ............................ 424/52; 106/35; 424/48; 424/49; 424/57; 424/602; 433/199.1; 433/215; 433/222.1; 433/228.1
[58] Field of Search ................... 433/199.1, 215, 433/228.1, 222.1; 106/35; 424/49, 48, 52, 57, 602

[56] References Cited

U.S. PATENT DOCUMENTS

| | | | |
|---|---|---|---|
| Re. 33,161 | 2/1990 | Brown et al. | 433/199.1 |
| Re. 33,221 | 5/1990 | Brown et al. | 433/199.1 |
| 1,225,362 | 5/1917 | Ruthrauff | 424/48 |
| 2,605,229 | 7/1952 | Marcus | 424/48 |
| 3,679,360 | 7/1972 | Rubin et al. | 424/48 |
| 3,913,229 | 10/1975 | Driskell et al. | 433/215 |
| 3,943,267 | 3/1976 | Randol | 424/49 |
| 4,048,300 | 9/1977 | Tomlinson et al. | 424/52 |
| 4,080,440 | 3/1978 | Diguilio et al. | 424/49 |
| 4,108,980 | 8/1978 | Duff | 424/52 |
| 4,143,128 | 3/1979 | Kim et al. | 424/54 |
| 4,144,324 | 3/1979 | Crutchfield et al. | 424/54 |
| 4,177,258 | 12/1979 | Gaffar et al. | 424/52 |
| 4,183,915 | 1/1980 | Gaffar et al. | 424/52 |
| 4,283,385 | 8/1981 | Dhabhar et al. | 424/52 |
| 4,327,079 | 4/1982 | Aoki | 424/49 |
| 4,342,741 | 8/1982 | Aoki | 424/49 |
| 4,348,381 | 9/1982 | Gaffar et al. | 424/52 |
| 4,397,837 | 8/1983 | Raaf et al. | 424/52 |
| 4,405,600 | 9/1983 | Besic | 424/57 |
| 4,515,770 | 5/1985 | Besic | 424/49 |
| 4,518,430 | 5/1985 | Brown et al. | 433/228.1 |
| 4,532,124 | 7/1985 | Pearce | 424/52 |
| 4,556,561 | 12/1985 | Brown et al. | 424/48 |
| 4,606,912 | 8/1986 | Rudy et al. | 424/52 |
| 4,610,873 | 9/1986 | Rudy et al. | 424/52 |
| 4,612,053 | 9/1986 | Brown et al. | 433/201.1 |
| 4,634,589 | 1/1987 | Scheller | 424/49 |
| 4,672,032 | 6/1987 | Slavkin et al. | 424/52 |
| 4,710,372 | 12/1987 | Scheller | 424/49 |
| 4,714,608 | 12/1987 | Rolla | 424/52 |
| 4,880,610 | 11/1989 | Constantz | 606/77 |
| 4,908,211 | 3/1990 | Paz | 424/440 |
| 4,923,683 | 5/1990 | Sakuma et al. | 424/52 |
| 5,034,059 | 7/1991 | Constantz | 424/423 |
| 5,037,639 | 8/1991 | Tung | 424/57 |
| 5,047,031 | 9/1991 | Constantz | 606/77 |
| 5,053,212 | 10/1991 | Constantz et al. | 606/53 |
| 5,129,905 | 7/1992 | Constantz | 606/76 |
| 5,145,668 | 9/1982 | Chow et al. | 424/52 |
| 5,268,167 | 12/1993 | Tung | 424/57 |

FOREIGN PATENT DOCUMENTS 2570292   3/1986   France.

OTHER PUBLICATIONS

Tung, et al. "Hydrolysis of Dicalcium Phosphate Dihydrate In The Presence Or Absence Of Calcium Fluoride" Basic Biol. Sciences: Dent, J. Res. 64(1): 2–5 Jan., 1985.

Patel, P. R., et al. "Solubility of $CaHPO_4 \times 2H_2O$ In The Quaternary System $Ca(OH)_2$—$H_3PO_4$—NaCl—$H_2O$ at 25° C." J. Res. Nat. Bur. Stand Nov.–Dec. 1974, pp. 675–681.

Brown, W., et al. "Crystallography Of Tetracalcium Phosphate" J. Res. Nat. Bur. Stand. 69A 547–551 (1965).

Moreno, E., et al. "Stability of Dicalcium Phosphate Dihydrate In Aqueous Solutions and Solubility Of Octocalcium Phosphate" Soil Science Society Proceedings, 1960, pp. 99–102.

Gregory, T. M., et al, "Solubility of $CaHPO_4 \times 2H_2O$ in the System $Ca(OH)_2$—$H_3PO_4$—$H_2O$ at 5, 15, 25, and 37.5° C." J. Res. Nat. Bur. Stand 74A 461–475 (1970).

Driskell, et al. "Development of Ceramic and Ceramic Composite Devices For Maxillofacial Applications" J. Biomed. Mater. Res. Symposium No. 2 (Part 2), 1972, pp. 345–361.

Markovic, et al. "Precipitation of Amorphous Calcium Strontium Phosphates" J. Dental Research, vol. 73, Special Issue, 1994.

McDowell, et al. " Solubility of $Ca_5(PO_4)_3 \times$In The System $Ca(OH)_2$—$H_3PO_4$—$H_2O$ at 5, 15, 25 and 37° C." J. Res. Nat. Bur. Stand, 81A 273–281 (1977).

Gregory, T. M. et al. "Solubility of B—$CA_3(PO_4)_2$ In The System $Ca(OH)_2$—$H_3PO_4$—$H_2O$ at 5, 15, 25 and 37° C." J. Res. Nat. Bur. Stand. 78A 667–674 (1974).

Levine, R. S. et al. "Remineralisation Of Natural Carious Lesions Of Enamel In Vitro" Brit. dent. J., 1974; 137, 132 Dental Caries Dental Enamel: Hydroxyapatide: 132–134.

Zimmerman, et al. "The Effect Of Remineralization Fluids On Carious Lesions In Vitro" IADR Abstract No. 282 (1979).

Silverstone, et al. "Progressions Of Caries–like Lesions In Vitro After Exposure To Synthetic Calcifying Fluids" IADR Abstract No. 283 (1979).

(List continued on next page.)

Primary Examiner—Ronald W. Griffin
Attorney, Agent, or Firm—Banner & Allegretti, Ltd.

[57] ABSTRACT

This invention involves new compositions and methods of use and delivery of amorphous strontium compounds such as: amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF) and amorphous strontium calcium carbonate phosphate fluoride (ASCCPF) for use in remineralizing and fluoridating teeth. These amorphous compounds or solutions which form the amorphous compounds, when applied either onto or into dental tissue prevent and/or repair dental weaknesses such as dental caries, exposed roots and dentin sensitivity.

27 Claims, No Drawings

OTHER PUBLICATIONS

Wefel, J. S., et al. "Artificial Lesion Formation In TiF$_4$ and APF Treated Enamel" IADR Abstract No. 284 (1979).

Crall, J. J., et al. "Artificial Lesion Formation and Progression after Two-step Topical Fluorides" IADR Abstract No. 285 (1979).

Hiatt, W. H., et al. "Root Preparation I. Obturation of Dentinal Tubules In Treatment Of Root Hypersensitivity:" J. Peridontal: 373–380 (1972).

Gelhard, T. B. F. M., "Rehardening Of Artificial Enamel Lesions In Vivo" Caries Res. 13: 80–83 (1979).

Silverstone, "Remineralization Phenomena" Caries Res. 11 (Suppl. 1): 59–84 (1977.

Briner, W. W., "Significance Of Enamel Remineralization" 53 239–243 (1974).

NASA And Dentistry, "New Tooth Enamel From Brushite Crystals" (Oct., 1977).

Pickel, F. D. "The Effects Of A Chewing Gum Containing Dicalcium Phosphate On Salivary Calcium And Phosphate" Ala. J.Med: 286–87 (1965).

Trautz, "Crystallographic Studies Of Calcium Carbonate Phosphate" Annals of the N.Y. Acad. Sci. 35, Article 1: 145–160 (1960).

Blumenthal, N. C. et al., "Effect Of Preparation Conditions On The Properties And Transformation Of Amorphous Calcium Phosphate" Mat. Res. Bull. 7: 1181–1190 (1972).

Posner, A. S. et al. "Synthetic Amorphous Calcium Phosphate And Its Relation To Bone Mineral Structure" Accts. Of Chem. Res. 8 273–281 (1975).

Tung, M. S., et al. "An Intermediate State In Hydrolysis Of Amorphous Calcium Phosphate" Calcif Tissue Int. 783–790 (1983).

LaGeros, R. Z., "Apatitic Calcium Phosphates: Possible Dental Restorative Materials" IADR Abstract No. 1482 J. Dent. Res. 61 (1982).

Tung, M. S., et al. "The Effects of Calcium Phosphate Solutions on Permeability of Dentin" J. Dent. Res., 65 Abstract No. 167 (1986).

Brown, et al., "Singular Points in the Chemistry of Teeth," IADR Abstract No. 120, J. Dent. Res. 54:74 (1975).

Guide To Dental Materials And Devices, 7 Ed. p. 49 (ADA 1974).

Ababa Takaaki, et al. "Small–Angle X-Ray Scattering Study On The Transformation Of Amorphous Calcium Phosphate To Crystalline Apatitie," Chem. Abstracts, vol. 91 No. 13, Abstract No. 105934q (1979).

Ababa Takaaki, "X–Ray Diffraction Study On The Amorphous And Crystalline Components In Bone Mineral" Chem. Abstracts, vol. 91, No. 13, Abstract No. 1 (1979).

Termine, John D., et al. "Calcium Phosphate In Vitro" Chem. Abst. vol. 73 Abstract No. 126985a (1970).

Hong, Y. C., et al. (1989): "The Periapical Tissue Reactions To A Calcium Phosphate Cement In The Teeth Of Monkeys," J. Dent. Res. (submitted).

McDowell, et al., "Solubility Study Of Calcium Hydrogen Phosphate. Ion–Pair Formation," Inorg. Chem. 10:1638–1643 (1971).

Tung, et al. "Effects of Calcium Phosphate Solutions on Dentin Permeability" vol. 19 No. 8, J. of Endodontic (1983).

Brown, "Solubilities of Phosphates and Other Sparingly Soluble Compounds" from Griffith, et al., Environmental Phosphorous Handbook (John Wiley & Sons New York 1973).

DeRijk, et al (1986) "Clinical Evaluation of an Hydroxyapatite Precipitate for the Treatment of Dentinal Hypersensitivity," Biomedical Engineering V. Recent Developments, Proc of 5th Southern Biomedical Engineering Conference. Subrata Saha, Ed., New York: Pergamon Press, pp. 336–339.

Lu, et al., (1988) "New Attachment Following the Use of a Novel Calcium Phosphate System" J. Dent. Res. 67:352, Abst. No. 1913.

Schreiber, et al. (1988) "Remineralization of Root Caries Lesion by a Calcium Phosphate Slurry," J. Dent. Res. 67:Abst. No. 255.

Sugawara, et al. (1987) "A Calcium Phosphate Root Canal Sealer–Filler" J. Dent. Res. 66:296 Abst. No. 1516.

Sugawara et al. (1988) "Formation of Hydroxyapatite in Hydrogels from Tetracalcium Phosphate/Dicalcium Phosphate Mixtures," J. Dent. Res. submitted.

Matsuya et al. "Effects of pH on the Reactions of Tetracalcium Phosphate and Dicalcium Phosphate" IADR Abstracts 1991.

Tamotsu et al. "Synthesis and Characteristics of Amorphous Calcium Carbonate in Ethanol" Chem. Sb. vol. 103, No. 18 (1985).

METHODS AND COMPOSITIONS FOR MINERALIZING AND/OR FLUORIDATING CALCIFIED TISSUES WITH AMORPHOUS STRONTIUM COMPOUNDS

This invention was made in the course of research, supported partially by the Government under grant DE 08916, awarded by the National Institute of Dental Research. The Government may have certain rights in the invention.

This is a continuation in part of application Ser. No. 08/104,350, filed Aug. 9, 1993, now U.S. Pat. No. 5,437,857; which is a divisional of application Ser. No. 07/723,839, filed Jul. 1, 1991, now U.S. Pat. No. 5,268,167; which is a divisional of application Ser. No. 07/356,201, filed May 24, 1989, now U.S. Pat. No. 5,037,639.

BACKGROUND OF THE INVENTION

1. Field of the Invention

This invention relates to certain amorphous compounds that are unique in their applications as remineralizers of caries lesions, cavities and root erosions of the tooth and desensitization of dentin. These amorphous compounds when further containing a fluoride compound can also be used for topical fluoridation of the teeth. When used for either fluoridation or mineralization these compounds prevent further tooth decay and actually restore the lesions caused by dental caries. This invention particularly involves the use of amorphous calcium compounds, the strontium substituted counterparts to the amorphous calcium compounds, and incorporation of magnesium to the amorphous compounds for the treatment of dental tissue.

The invention is further directed to methods for delivering these amorphous compounds to dental tissue. It has been found that carbonated solutions are especially effective in such delivery and may be used to control the pH and stability of the solutions. These carbonated solutions precipitate calcium and/or strontium compounds when applied under oral conditions due to the escape of dissolved carbon dioxide and the increase in the pH of solutions.

2. Description Of The Prior Art

When an incipient lesion or cavity develops on the surface of a tooth, the dentist traditionally fills the cavity that forms. This procedure may prevent the decay from spreading further, but does not restore the tooth to its original state.

Dental lesions and cavities, exposed roots and dentin sensitivity develop due to the loss of tooth minerals. Tooth minerals are apatites that are impure forms of hydroxyapatite, $Ca_5(PO_4)OH$. Recently, the processes of topical fluoridation and mineralization have been used and developed to treat these dental maladies. The objectives of topical fluoridation and mineralization are to deposit fluoride and apatite on and into the tooth, thus preventing further tooth decay, restoring the tooth or obturating the dentinal tubules.

Three approaches have been used for topical fluoridation of the tooth. The first introduces simple fluoride-containing compounds onto the surface of the dental enamel. The second one introduces acidulated phosphate fluoride, which involves the dissolution of some tooth tissue and precipitation of calcium fluoride. The third procedure involves an intermediate product of dicalcium phosphate dihydrate which then converts to fluorapatite.

A considerable amount of research has recently been directed toward the remineralization of dental lesions. In the area of remineralization of dental tissues, there are at least three approaches. One uses a metastable fluoride-containing calcium phosphate solution supersaturated with respect to fluorapatite and hydroxyapatite which will form apatite slowly when applied. A second uses combinations of sparingly soluble calcium phosphates with crystallized tetracalcium phosphate and at least one different calcium phosphate in slurries and paste forms. Such an application is disclosed in U.S. Pat. No. 4,612,053 to Brown, et. al. A third uses potassium oxalate solutions to obturate the dentinal tubules as disclosed in U.S. Pat. No. 4,538,990, issued to Pashley, et. al., and U.S. Pat. No. 4,057,621, issued to Pashley, et. al.

These prior art mineralization methods are characterized by several practical problems. When a supersaturated solution of low calcium and phosphate concentrations is used, the remineralization process is extremely slow. The remineralization process is, in fact, so slow that an inconvenient amount of time is required for its completion. Another problem with these methods is that as the apatite is deposited upon the teeth, the pH's of the treating solutions change. Such a change can make the solution too acidic, creating the possibility of damaging the dental tissue.

Therefore, there remains a need for a treatment which achieves rapid remineralization of teeth similar to the natural process of biological mineralization, without the dissolution of the existing dental tissue.

Although the prior art does not teach the use of amorphous calcium compounds for remineralization of teeth, it does refer to amorphous calcium phosphate as an aspect of the investigation of natural bone formation. See *Synthetic Amorphous Calcium Phosphate and Its Relation to Bone Mineral Structure*, Posner and Betts, ACCOUNTS OF CHEMICAL RESEARCH, Jan. 31, 1975; *An Intermediate State in Hydrolysis of Amorphous Calcium Phosphate*, Tung and Brown, CALCIFIED TISSUE INTERNATIONAL, 1983. This use, however, is significantly different from the present invention. Bone tissue is 50% organic material and 50% inorganic material, whereas dental tissue is 90% inorganic. As such, significantly different factors affect the treatment of the different tissues.

The prior art further teaches the use of amorphous tricalcium phosphate as surgical cement in teeth and bones. See U.S. Pat. No. 4,684,673 issued to Adachi. Contrary to the present invention, Adachi teaches a filler or a cement, not a composition which reconstructs the dental tissue.

Moreover, strontium compounds have been used in dental preparations before. Topical application of 25% strontium chloride in aqueous solution has been used for desensitization with considerable success. Additionally, dentifrice with strontium chloride has been used to reduce the hypersensitivity of dentin commercially. But there is no teaching of any use of amorphous strontium compounds as dental remineralizers in the prior art.

SUMMARY OF THE INVENTION

The potential for application of dental remineralization is vast. Dentists fill millions of cavities each year. If these cavities were remineralized at early stages rather than filled the general dental health of the public would be increased substantially, since remineralization results in a whole tooth. The present invention seeks to provide remineralization compositions and methods that can practically be applied under a dentist's care and decrease the need for filling of the teeth.

This invention involves the use of novel remineralization materials for remineralization of teeth and novel methods for delivering these materials to the teeth and regulating their deposition in and onto the teeth. This invention involves the use of amorphous calcium compounds such as: amorphous calcium phosphate (ACP), amorphous calcium phosphate fluoride (ACPF) and amorphous calcium carbonate phosphate (ACCP) for use in remineralizing teeth. These amorphous compounds when applied either onto or into dental tissue prevent and/or repair dental weaknesses such as dental caries, exposed roots and sensitivity. The compounds have the highest solubilities, fastest formation rates and fastest conversion rates (to apatite) among all the calcium phosphates under physiological conditions. Moreover, in the presence to fluoride the amorphous compounds convert rapidly to fluoride containing apatite.

This invention is also directed to the use of amorphous strontium compounds such as: amorphous strontium phosphate (ASP), amorphous strontium phosphate fluoride (ASPF), amorphous strontium calcium phosphate (ASCP), amorphous strontium calcium carbonate phosphate (ASCCP), amorphous strontium carbonate phosphate fluoride (ASCPF), and amorphous strontium calcium carbonate phosphate fluoride (ASCCPF) in remineralizing teeth. These amorphous compounds when applied either onto or into dental tissue prevent and/or repair dental weaknesses such as dental caries, exposed roots and sensitivity. The compounds have higher solubilities, faster formation and conversion rates (to apatite) than crystalline calcium phosphates and corresponding amorphous calcium phosphates under physiological conditions. Moreover, in the presence of fluoride the amorphous compounds convert rapidly to fluoride containing apatite.

In addition to the amorphous compounds and the use of those compounds to treat dental tissue, the present invention includes compositions and methods for delivering the amorphous compounds and other beneficial substances, such as chlorhexidine, potassium nitrate, or ethanol, to the surface to be treated. These methods and compositions take advantage of the increased solubility of the compounds in acidic, low pH, solutions. Moreover, the acidity of the solutions is controlled through the control of the conversion reaction between carbonic acid and carbon dioxide. These methods and compositions allow for the delivery of an effective quantity of treatment material to the surface to be treated.

It should be understood that while the delivery methods of the present invention were created in relation to the treatment of dental tissue, the method has applicability and advantages in other areas as well.

The advantages of the use of the amorphous compounds according to the present invention as compared to the solutions and slurries of the prior art are many. Most importantly, the use of the compounds and methods of the invention allows for the most rapid deposition of tooth mineral upon dental tissues. Therefore, remineralization of the teeth can be achieved more quickly. In addition, the present invention provides for remineralization and fluoridation simultaneously when the amorphous calcium compound contains a fluoride.

Another significant advantage is that the present invention will not damage the teeth due to a large change in pH during the remineralization process.

Yet another advantage of the present invention is that it provides compositions and methods which can practically be used in remineralization without long term or excessive repeated treatments.

Yet a further advantage of the present invention is the provision of a composition for remineralization of teeth which can be easily formulated and easily applied to the teeth.

Still a further advantage of the present invention is the provision of a composition for remineralization and desensitizing of the dental tissue.

Thus, the present invention provides compositions and methods for remineralization of caries lesions that are practical for the use in a clinic or home environment. The invention also provides compositions and methods for the rapid fluoridation of teeth by the use of amorphous calcium fluoride and amorphous strontium calcium fluoride compounds. Through either of these processes damaged dental tissues can be quickly and easily repaired, restoring the tooth to a whole healthy tooth.

Further objects of the inventions will become apparent with the following description of the preferred embodiments and claims.

DETAILED DESCRIPTION OF THE PREFERRED EMBODIMENTS

The inventor has found that amorphous calcium phosphate (ACP), amorphous calcium phosphate fluoride (ACPF), and amorphous calcium carbonate phosphate (ACCP) are solid solutions with variable compositions. These solutions have no long range structure; however, they are homogeneous when measured on the molecular scale. Under physiological conditions these amorphous calcium compounds have high solubilities, high formation rates and high rates of conversion to apatite. The high rate of conversion to apatite allows the remineralization to take place at a greater speed. This speed allows for a practical method for remineralization of dental tissue without an undue number of treatments. Moreover, in the presence of fluoride, the amorphous compounds convert to fluoride-containing apatite.

The inventor has also found that strontium ions can isomorphically replace calcium ions in calcium phosphates and amorphous calcium compounds. Moreover, it has been discovered that strontium compounds such as strontium phosphates and strontium fluoride have higher solubilities than respective calcium compounds. Amorphous strontium compounds have the highest solubilities, fastest formation rates and conversion rates (to apatite) among all the calcium phosphate and strontium phosphates under physiological conditions making amorphous strontium compounds excellent materials for mineralization and fluoridation. It will be appreciated that the term "apatite," as used herein, includes pure apatite, strontium containing apatite and apatite containing both strontium and calcium.

Furthermore, the inventor has found that the magnesium ions, either incorporated into the amorphous compounds or in the solution that forms the amorphous compounds, can regulate the precipitation, dissolution and conversion of the amorphous compounds. Therefore, the presence of magnesium ions is useful in mineralizing and/or fluoridating calcified tissues.

The driving forces behind the precipitation of the amorphous calcium compounds, the amorphous strontium and apatite compounds from solutions are the temperature and the pH of the solution. At lower pH and temperature, strontium and calcium phosphate solutions are capable of supporting higher calcium, strontium and phosphate concentrations. Therefore, as the pH or the temperature rises, the solutions become supersaturated. In this supersaturated state the solutions can rapidly precipitate amorphous phosphate compounds or apatite onto a tooth. This property indicates that carbonated solutions containing strontium, calcium, fluoride, carbonate and phosphate ions provide advantageous compositions and methods for delivery and deposition of amorphous phosphate and/or apatite to needed sites, because of the pH control and the stability of the solutions. Specifically, due to the escape of carbon dioxide from the carbonated solution, the pH will increase and precipitation of beneficial ions will occur.

Remineralization is accomplished by bringing the amorphous compound into contact with the dental tissue. This can be done directly, i.e., putting an amorphous compound directly on the tooth, or indirectly through a carrier, i.e., incorporating the amorphous compound in an aqueous or nonaqueous carrier such as a gel, a chewing gum, a polymer matrix, a candy or other confectionary, or a toothpaste and applying the carrier to the dental tissue. Once contact is established, deposition of calcium phosphate results from the rise in pH and temperature brought on by oral conditions. Once deposited on the dental tissue the calcium phosphate will recrystallize in situ and reform the tooth.

In another embodiment of the invention, the amorphous compounds are formed, in situ, as an intermediate prior to the formation of the apatite. Such an embodiment includes carbonated solutions containing calcium ions, strontium ions, fluoride ions, carbonate ions and phosphate ions, maintained under a pressurized carbon dioxide atmosphere. The solution also preferably contains a cariostatic agent, a stabilizing agent, and an adhesion enhancing agent. Under the pressurized carbon dioxide atmosphere, the solutions have a lower pH and are stable. When applied under oral conditions, carbon dioxide escapes, causing the pH to increase. This increase in pH results in a supersaturated solution and ultimately rapid precipitation of amorphous phosphate compounds or apatite. Specifically, the ACP, ACPF, ACCP, ASP, ASPF, ASCP, ASCCP, ASCPF or ASCCPF precipitate on and into the dental tissue due to the increases in instability and precipitation rate as temperature and pH of the solution increase.

The pH and degree of supersaturation (with respect to amorphous tricalcium phosphate) of one composition containing 16 mM of calcium chloride, 0.6 mM of potassium phosphate and 0.1 mM of potassium fluoride is shown in Table I (below) before and after application. Before application, the composition was held under 1.5 atmosphere pressure of carbon dioxide and at 4° C.; after application, it was under normal atmosphere (0-0.01 atm) and 35° C.

TABLE 1

The pH and degree of supersaturation (with respect to amorphous tricalcium phosphate) of the solution before and after application.

| | Temp. °C. | pH | $CO_2$ Pressure (atm) | Total Carbon (mM) | Degree of Saturation |
|---|---|---|---|---|---|
| Before | 4 | 4.5 | 1.5 | 111 | undersaturation |
| After | 37 | 10.0 | 0 | 0 | $10^{5.0}$ |
| | | 7.75 | 0.005 | 5.69 | $10^{3.1}$ |
| | | 7.5 | 0.01 | 6.44 | $10^{2.6}$ |

Another feature of the invention is its capacity to fluoridate the dental tissue. When the amorphous calcium strontium compounds exist in the presence of fluoride ions, fluoride containing apatite is precipitated. The beneficial effects of fluoride in dental tissue are well known.

As indicated above, the pH is one of the factors that controls the rate of the conversion to and deposition of apatite in and onto the teeth. Therefore, it is desirable to regulate the acidity of the solution and control the reaction. It has been discovered that the acidity (pH) of the solution can be regulated by controlling the conversion reaction between carbon dioxide and carbonic acid. The conversion reaction is shown below:

$$CO_2 + H_2O \longleftrightarrow H_2CO_3$$

The above equation indicates the acidity of a system can be controlled by controlling the concentration of $CO_2$. As the concentration of $CO_2$ increases, the reaction is driven to the right and the solution becomes more acidic and, conversely, as the $CO_2$ concentration in the atmosphere decreases the reaction will be driven to the left and the acidity will decrease.

An application where the control of the pH through the control of the $CO_2$ is especially useful is in the precipitation of materials, including apatite and chlorhexidine, From pressurized carbonated solutions or aerosols (liquid gas systems). In such a system, the pressurized carbon dioxide drives the conversion reaction to the right and maintains the solution in an acidic state by generating carbonic acid. As the carbon dioxide is removed by exposure of the solution to the atmospheric conditions, carbonic acid will convert to carbon dioxide and the solution will become less acidic. As the solution becomes less acidic the desired material, such as apatite or chlorhexidine, is precipitated out of solution. Therefore, this system is especially appropriate for delivering compounds that have high solubility in acidic solution and precipitate out of solution in more basic conditions. Materials such as amorphous calcium compounds, amorphous strontium compounds and synthetic saliva can be delivered to the mouth in this way and precipitated into and onto the teeth. The synthetic saliva preferably contains the same or higher concentrations of calcium and phosphate ions as natural saliva. The materials in one preferred embodiment would also include a fluoride source, either simple or complex fluoride, in the pressurized carbonated solution to fluoridate the teeth. Such complex fluorides include hexafluorosilicate, monofluorophosphate and hexafluorostannate.

The pressurized carbonated solutions of amorphous strontium calcium compounds of the present invention have the additional advantage of being useful for treating the dentin surface of the tooth to improve the bonding of the restorative material, for example amalgams or plastics (see, Bowen patents, U.S. Pat. Nos. 4,514,527; 4,521,550; 4,588,756; 4,659,751), in conventional dental restorations. It has been found that application of these pressurized carbonated solutions to the etched dentin in preparing for restoration will improve the bond strength between the dentin and the restorative material. The pressurized acidic carbonated solution also may be used to dissolve the smear layer of dentin surface, due to its acidity. Some of the dissolved apatite will remineralize the dentin after the escape of carbon dioxide and the increase of pH.

It has also been found to be desirable to deliver chlorhexidine into the mouth for the treatment of dental surfaces. Chlorhexidine is an antiseptic agent which has the known characteristics of aiding in the prevention of gum disease. However, delivery of chlorhexidine itself to the dental tissue in effective amounts has been difficult. Chlorhexidine is a base which is only slightly soluble in water under normal conditions. This solubility increases thirty times when the solution is maintained under a carbon dioxide atmosphere of 160 psi. Therefore, the pressurized carbonated solution described above is particularly effective in delivering chlorhexidine to the dental surface. It has been found that alcohol, preferably ethanol, increases the solubility of chlorhexidine. Thus, the addition of ethanol to the pressurized carbonated solution will further increase the effectiveness of the solution in delivering chlorhexidine to the dental tissue. The addition of ethanol also affects the solubility and precipitation of alkaline earth phosphates, such as calcium phosphates.

In addition to the amorphous calcium compounds, amorphous strontium compounds and/or chlorhexidine discussed above, the pressurized carbonated solution may contain other beneficial substances. In particualr, one embodiment of the invention includes a carbonated solution that includes a gelling compound, such as polyvinylalcohol. Furthermore, gelling compounds which form gel as the acidity of the solution decreases, i.e., as the carbon dioxide escapes from the solution, are especially useful. The other compounds precipitating out of the solution, e.g., amorphous strontium compounds, will thus be suspended within the dental tissue thus increasing the efficiency of the remineralization and fluoridation process.

Other beneficial substances that may be included in the compounds of the present invention include desensitizing agents. Fluoride is a known desensitizing agent. Thus, the fluoride containing amorphous compounds discussed earlier are effective in desensitizing dental tissue. Other desensitizing agents that may be incorporated include potassium nitrate and strontium chloride.

It should be understood that the system using pressurized carbonated solutions to control the acidity of the solution is applicable in arts other than the dental arts. For example, the system would be advantageous for the delivery of monomers which are stable in acidic solutions but polymerize in a basic solution.

A further use of the control of acidity of a reaction system through the control of the carbon dioxide-carbonic acid conversion reaction in a solid-solution-gas system is illustrated in the following reaction:

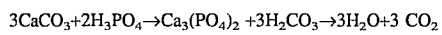
$$3CaCO_3 + 2H_3PO_4 \rightarrow Ca_3(PO_4)_2 + 3H_2CO_3 \rightarrow 3H_2O + 3\ CO_2$$

The above reaction illustrates how controlling the acidity of a reaction system through control of the carbon dioxide concentration can aid in generating a desired precipitate from acidic solid-solution-gas systems. In the above reaction a carbonate salt and an acid (or acidic salt) are dissolved in solution and make the solution acidic initially. As the carbonic acid forms, it escapes from solution as carbon dioxide. As acidity decreases the desired material, calcium phosphate is precipitated out of solution.

The principles of this reaction are especially applicable in nonaqueous carriers, such as a gel, a polymer, a powder, a chewing gum, candy or other confectionary or a toothpaste. The carbonate salt and the acid (or acidic salt) can be suspended within the gel, the polymer, the toothpaste or the chewing gum to create a nonaqueous dispersion. Upon contact with an aqueous solution, such as saliva within the mouth, the reaction between the carbonate and the acid is initiated resulting in deposition of the desired material. The desired material could be either amorphous strontium compounds or more conventional remineralization materials.

Another method of using $CO_2$ to control the pH of solution is the application of the fact that a stable alkaline solution can contain high concentration of carbonate under atmospheric condition. An aqueous carbonated calcium strontium phosphate solution supersaturate with respect to calcium strontium phosphates and carbon dioxide under atmospheric condition can be prepared by mixing a stable alkaline solution containing carbonate with a stable acidic solution containing calcium and strontium ions and either or both solutions further contains phosphate ions. Because of the supersaturated nature of the mixed solutions, strontium calcium phosphate compounds will precipitate of the mixed solution as the pH of the solution changes due to the release of carbon dioxide. Therefore, when the mixed solution is put in the mouth, carbon dioxide will be released, and the desired compound will precipitate on and in the teeth.

This invention provides the compositions that contain ACP, ACPF, ACCP and methods that deposit the ACP, ACPF, or ACCP on and into the tooth. The compositions are ACP, ACPF, ACCP themselves or solutions containing calcium, fluoride, carbonate and phosphate so that will form ACP, ACPF, or ACCP when applied. Upon application, ACP, ACPF, or ACCP remineralize and/or fluoridate the tooth and, in the case of exposed root and dentin sensitivity, obstruct the dentinal tubules and desensitize the tooth. Thus, use of the compositions in accord with this invention provides relief to damaged dental tissue.

This invention further provides the compositions that contain ASP, ASPF, ASCP, ASCCP, ASCPF and ASCCPF and methods that deposit the ASP, ASPF, ASCP, ASCCP, ASCPF or ASCCPF on and into the tooth. The compositions are ASP, ASPF, ASCP, ASCCP, ASCPF or ASCCPF themselves or solutions containing strontium, calcium, phosphate, carbonate, and/or fluoride that will form ASP, ASPF, ASCP, ASCCP, ASCPF or ASCCPF when applied. Also, the above amorphous strontium compounds can be in the form of gel composed of strontium, calcium and phosphate. Upon application, ASP, ASPF, ASCP, ASCCP, ASCPF or ASCCPF remineralizes and/or fluoridates the tooth and, in the case of exposed root and dentin sensitivity, obstruct the dentinal tubules and desensitize the tooth. Thus, use of the compositions in accord with this invention provides relief to damaged dental tissue.

The following examples serve to illustrate preparation and use of the compositions of the present invention.

EXAMPLE 1

A gel, powder, polymer, or aqueous or nonaqueous solution, containing an amorphous calcium compound (such as ACP, ACPF, or ACCP) alone or together with other beneficial ingredients such as fluoride was applied on the tooth surface. The ACP, ACPF, or ACCP was prepared in two ways: (1) ACP, ACPF or ACCP powder was first prepared by rapid mixing of high concentrations of calcium and phosphate (with or without fluoride or carbonate) at high pH (>9.0), filtration and drying; ACP, ACPF or ACCP powder was then suspended in the solution or gel; or (2) Rapid mixing of two solutions, one containing a high concentration of calcium ion such as 1.5M $Ca(NO_3)_2$, the other containing a high concentration of phosphate such as 1.5M $K_3PO_4$ with or without fluoride or carbonate, produced ACP, ACPF or ACCP.

EXAMPLE 2

A solution or gel containing a high concentration of phosphate (such as 1.5M $K_3PO_4$) with high pH ($\geq 9$) and 1000 ppm fluoride was applied to tooth surface for 1 min., followed by application of a solution or gel containing a high concentration of calcium ions (such as 1.5M $Ca(NO_3)_2$). The combination of the two solutions result in the formation of amorphous calcium compounds on and into the tooth. The amorphous calcium compounds then convert to fluoride containing apatite.

EXAMPLE 3

A carbonated cold solution or gel (5° C. and under pressurized carbon dioxide atmosphere) is prepared containing a high concentration of calcium, $PO_4$ and F. The solution also contains cariostatic agents, strontium and tin, an adhesive enhancing agent, oxalate, and stabilizing agents such as macromolecules (polylysine or carboxy methyl cellulose) and/or hydroxyethane diphosphonate. The solution is then applied on the tooth surface. The carbon dioxide escapes from the solution under oral atmosphere and the pH of the solution increases. As ions diffuse into the tooth, they leave behind the stabilizing agents and into a milieu of higher temperature. This results in an increasingly unstable solution and rapid precipitation.

The carbonated cold solution or gel may also be prepared by mixing two cold solutions under carbon dioxide atmosphere just before the application. One solution would contains calcium and other beneficial cations and ingredients, and the other solution would contains phosphate, fluoride and other beneficial anions and ingredients.

EXAMPLE 4

Chewing gum is prepared containing ACP, ACPF or ACCP as prepared in example 1, with or without fluoride.

EXAMPLE 5

Solid powders containing mixtures of calcium salts and phosphate salts with or without fluoride or carbonate salts such as 0.33 g calcium chloride, 0.42 g potassium phosphate and 0.02 g sodium fluoride, are applied directly to the tooth, used as pumice flour, or dispersed in gel, chewing gum or other nonaqueous mediums such as toothpaste which is placed in contact with the tooth. These powders are easily dissolved in saliva and then reprecipitated as ACP, ACPF or ACCP in and on the tooth.

EXAMPLE 6

A carbonated beverage or mouth rinse contains calcium ions, phosphate ions, and other ingredients which forms ACP, ACPF, or ACCP in conditions simulating the oral cavity.

EXAMPLE 7

A gel, powder, polymer, or aqueous or nonaqueous solution containing ASP, ASPF, ASCP, ASCCP or ASCCPF alone or together with other beneficial compounds such as fluoride was applied on the tooth surface. The ASCP, ASCCP or ASCCPF was prepared in two ways: (1) ASCP, ASCCP or ASCCPF powder was first prepared by rapid mixing solutions with high concentrations of strontium, calcium and phosphate (with or without fluoride and/or carbonate) at high pH (>9.0). The resulting mixed solution was then filtered and dried resulting in ASCP, ASCCP or ASCCPF powder; (2) Rapid mixing of two solutions, one containing a high concentration of strontium and calcium ions such as 1.5M $Sr(NO_3)_2$ and $Ca(NO_3)_2$, the other containing a high concentration of phosphate such as 1.5M $K_3PO_4$ with or without calcium, fluoride or carbonate, produced ASCP, ASCCP or ASCCPF.

EXAMPLE 8

A dentifrice contains 5% amorphous strontium calcium carbonate phosphate fluoride (ASCCPF), when applied on the tooth, will dissolve and releases strontium, calcium, bicarbonate, phosphate and fluoride.

EXAMPLE 9

A solution or gel containing a high concentration of phosphate (such as 1.5M $K_3PO_4$) with high pH (>9) and 1000 ppm fluoride was applied to tooth surface for 1 min. followed by application of a solution or gel containing a high concentration of strontium and calcium ions (such as 1.5M $Sr(NO_3)_2$ and $Ca(NO_3)_2$).

EXAMPLE 10

Chewing gum contained amorphous strontium compounds with or without fluoride.

EXAMPLE 11

Solid powders containing mixtures of strontium salts, calcium salts and phosphate salts with or without fluoride or carbonate salts such as 0.635 g strontium nitrate, 0.333 g calcium chloride, 0.425 g potassium phosphate and 0.021 g sodium fluoride, were applied directly to the tooth, used as pumice flour, or dispersed in gel, chewing gum or other nonaqueous mediums such as toothpaste or polymer. These powders were easily dissolved in saliva and then precipitated as amorphous strontium compounds in and on the tooth. Alternatively, the solid powders above can be dissolved in water, and the resulting solution used as a mouth rinse.

EXAMPLE 12

A carbonated cold solution or gel (5° C. and under pressurized carbon dioxide atmosphere) containing a high concentration of strontium, calcium, phosphate and fluoride together with other beneficial ions such as chlorohexidine, tin, oxalate, alcohol, etc., and stabilizing agents such as macromolecules and/or hydroxyethane diphosphonate was applied on the tooth surface. The carbon dioxide escaped from the solution under oral atmosphere and the pH of the solution increased. As ions diffused into the tooth, they left behind the stabilizing agents and into the milieu of higher temperature. The amorphous strontium compounds precipitated on and into the teeth due to the increases in instability and precipitation rate in the absense of stabilizing agents as temperature and pH of solution increased. The carbonated cold solution or gel may also be prepared by mixing two cold solutions under carbon dioxide atmosphere just before the application; one solution contains strontium, calcium and other beneficial cations, and the other solution contains phosphate, fluoride and other beneficial anions.

The preferred embodiment of the present invention is now fully described. The above description, however, is only illustrative of the invention and is not intended to limit the invention in spirit or scope. Only the following claims and their equivalents limit the scope of the invention.

I claim:

1. A method for treating and remineralizing teeth through the formation of mineral onto and into the dental tissue comprising contacting a dental restorative with the teeth, said dental restorative comprising in combination:

a carrier selected from the group of a gel, a polymer, a chewing gum, a powder, a mouth rinse, an aerosol, a carbonated solution, a candy, a confectionary or a toothpaste for suspension of amorphous strontium compounds; and amorphous strontium compounds or solutions which will form amorphous strontium compounds suspended within said carrier, whereby when the combination is applied to the teeth, the amorphous strontium compounds will precipitate into and on the teeth and form strontium containing apatite.

2. A method of claim 1, wherein the amorphous strontium compounds or solutions which will form amorphous strontium compounds further contain calcium ions.

3. A method of claim 2, wherein the amorphous strontium compounds are in the form of a gel.

4. A method of claim 1, wherein the amorphous strontium compounds or the solution which will form amorphous strontium compounds further contain magnesium ions.

5. The method according to claim 1 wherein the amorphous strontium compounds or the solution which will form amorphous compounds further contain a fluoride source.

6. The method according to claim 5 wherein the fluoride source is monofluorophosphate.

7. The method according to claim 5 wherein the fluoride source is hexafluorosilicate.

8. The method according to claim 5 wherein the fluoride source is hexafluorostannate.

9. The method according to claim 1 wherein the amorphous strontium compounds further contain carbonate, thereby causing bicarbonate to be formed upon the deposition of amorphous strontium carbonate phosphate compounds.

10. A pressurized carbonated solution containing ions that form amorphous strontium compounds, whereby, when the pressure is released and carbon dioxide is removed, the acidity of the solution decreases and the amorphous strontium compounds precipitate out of solution allowing for delivery of the compounds to a dental tissue.

11. The pressurized carbonated solution of claim 10 wherein the dental tissue is the dentin surface of the tooth which has been prepared to bond to a restorative material.

12. A method for treating dental tissue comprising contacting the pressurized carbonated solution in claim 11 to a dentin surface to improve the bonding between the dentin and restorative material.

13. The pressurized carbonated solution of claim 10 wherein the solution contains strontium, calcium, carbonate, phosphate and fluoride ions and the amorphous strontium compound is amorphous strontium calcium carbonate phosphate fluoride.

14. The pressurized carbonated solution of claim 13 wherein the fluoride is monofluorophosphate.

15. The pressurized carbonated solution of claim 10 also including chlorhexidine.

16. The pressurized carbonated solution of claim 10 further comprising ethanol.

17. The pressurized carbonated solution of claim 10 further including a gel.

18. The pressurized carbonated solution of claim 10 where the carbonated solution further includes a gelling agent, whereby gelling occurs as a result of the decrease in the acidity of the solution and the amorphous strontium compound is suspended within the resulting gel.

19. The pressurized carbonated solution of claim 10 further including a complex fluoride, whereby when the solution is applied to dental tissue and pressure is released, carbon dioxide escapes from the solution, the acidity of the solution decreases and the complex fluoride is hydrolyzed releasing simple fluoride onto and into the dental tissue.

20. The pressurized carbonated solution of claim 19 wherein the complex fluoride is hexafluorosilicate.

21. The pressurized carbonated solution of claim 19 wherein the complex fluoride is hexafluorostannate.

22. The pressurized carbonated solution of claim 19 further including a gelling agent, whereby gelling and hydrolysis of complex fluoride occur as a result of the decrease in the acidity of the solution and the fluoride is suspended within the resulting gel.

23. A method for treating and mineralizing a dentin surface to improve the bonding between dentin and restorative materials comprising applying the pressurized carbonate solution of claim 19 to the dentin surface.

24. A method for removing a smear layer and remineralizing a dentin surface comprising contacting the dentin surface with a pressurized acidic carbonated solution containing ions that will precipitate as amorphous strontium compounds upon reduction of the solution acidity.

25. A method for treating and remineralizing dental tissue comprising contacting the dental tissue with a dental restorative, said dental restorative comprising a gel of strontium calcium phosphate carbonate either formed on the tooth surface or immediately before application.

26. A method of preparing an aqueous carbonated strontium calcium phosphate solution supersaturated with respect to strontium calcium phosphate carbonate and carbon dioxide under atmospheric conditions for use in treatment of dental tissue, comprising mixing a stable alkaline solution containing carbonate with a stable acidic solution containing strontium and calcium ions and either or both solutions further contains phosphate ions.

27. A method for treating and remineralizing teeth through the formation of mineral onto and into the dental tissue comprising contacting a dental restorative with the teeth, said dental restorative comprising in combination:

a non-toxic carrier capable of suspension of amorphous strontium compounds or a material that will form amorphous strontium compounds therein; and amorphous strontium compounds or solutions which will form amorphous strontium compounds suspended within said carrier, whereby when the combination is applied to the teeth, the amorphous strontium compounds will precipitate into and on the teeth and form strontium containing apatite.

* * * * *